US00PP18390P3

(12) United States Plant Patent
Gerawan

(10) Patent No.: US PP18,390 P3
(45) Date of Patent: Jan. 1, 2008

(54) PEACH TREE NAMED 'GP45-11'

(50) Latin Name: *Prunus persica*
Varietal Denomination: GP45-11

(76) Inventor: Mike Gerawan, 21249 E. Jefferson, Reedley, CA (US) 93654

( * ) Notice: Subject to any disclaimer, the term of this patent is extended or adjusted under 35 U.S.C. 154(b) by 0 days.

(21) Appl. No.: 11/357,547

(22) Filed: Feb. 17, 2006

(65) Prior Publication Data

US 2007/0199116 P1 Aug. 23, 2007

(51) Int. Cl.
*A01H 5/00* (2006.01)

(52) U.S. Cl. ..... Plt./198
(58) Field of Classification Search ..... Plt./198
See application file for complete search history.

(56) References Cited

U.S. PATENT DOCUMENTS

PP2,964 P * 1/1970 Merrill ..... Plt./198
PP6,045 P * 10/1987 Jost ..... Plt./198

* cited by examiner

*Primary Examiner*—Kent Bell
*Assistant Examiner*—S. B. McCormick-Ewoldt
(74) *Attorney, Agent, or Firm*—Townsend and Townsend and Crew LLP

(57) ABSTRACT

A new and distinct variety of peach tree is characterized by producing a freestone fruit with good red coloration, and that is ripe for commercial harvesting and shipment between July 13–20 in the San Joaquin Valley of Central California. The new variety is closely similar to the 'O'Henry' peach tree (nonpatented) from which it is a bud sport and from which it is distinguishable in that the fruit matures earlier than the 'O'Henry' peach fruit, is more highly colored, has very good flavor and stores very well.

1 Drawing Sheet

Latin name of the genus and species: The peach cultivar of this invention is botanically identified as *Prunus persica.*

Variety denomination: The variety denomination is 'GP45-11'.

BACKGROUND OF THE INVENTION

During the continued efforts to improve the quality of available fruit for the consumer, the inventor discovered a bud sport of the O'Henry/Peach variety (U.S. Plant Pat. No. 2,964) on a block of peaches in August of 1999. The bud sport was taken from one tree. After reexamining the fruit in 2000, budwood was collected and budded on to 'Nemaguard' rootstock in the dormant season of 2000/2001 on current site, which is on the west side of the Central San Joaquin Valley, approximately 3½ miles south of Kerman, Calif. Enough trees (11,403) of this invention were asexually reproduced to plant 59–66 acres. The resulting fruit produced in this planting produced highly colored fruit, with very good size, two weeks before the 'O'Henry' variety. In addition this fruit is very juicy with good flavor. The fruit produced in all respects is identical to the original bud sport.

ORIGIN AND ASEXUAL REPRODUCTION

The present invention (variety) was discovered in an 'O'Henry' peach planting in August of 1999 on the west side of Madera Avenue, approximately 3½ miles south of the town of Kerman, Calif. in the San Joaquin Valley of Central California. The new variety was asexually reproduced in the dormant season of 2000/2001 by bud grafting on 'Nemaguard' rootstock. Enough trees were asexually reproduced to plant 59–66 acres of the new variety. The inventor carefully compared the asexually reproduced trees with the parent sport, including the fruit, and found they were identical in all respects.

BRIEF SUMMARY OF THE INVENTION

The 'GP45-11' peach is characterized by producing a large freestone fruit that has good blush coloration and is ripe for commercial harvesting and shipping around July 13–20 in a normal year in the San Joaquin Valley of Central California. This new variety is a large fruit with a red blush and yellow flesh with red flecks. It is most similar to the 'O'Henry' peach tree (nonpatented) from which it is a bud sport. However, it is distinguishable in that it ripens approximately two weeks before the 'O'Henry' variety. The fruit of this new variety is large, with good flavor and good red color, which makes it quite acceptable to the consumer.

DETAILED DESCRIPTION OF THE INVENTION

Figure 1:
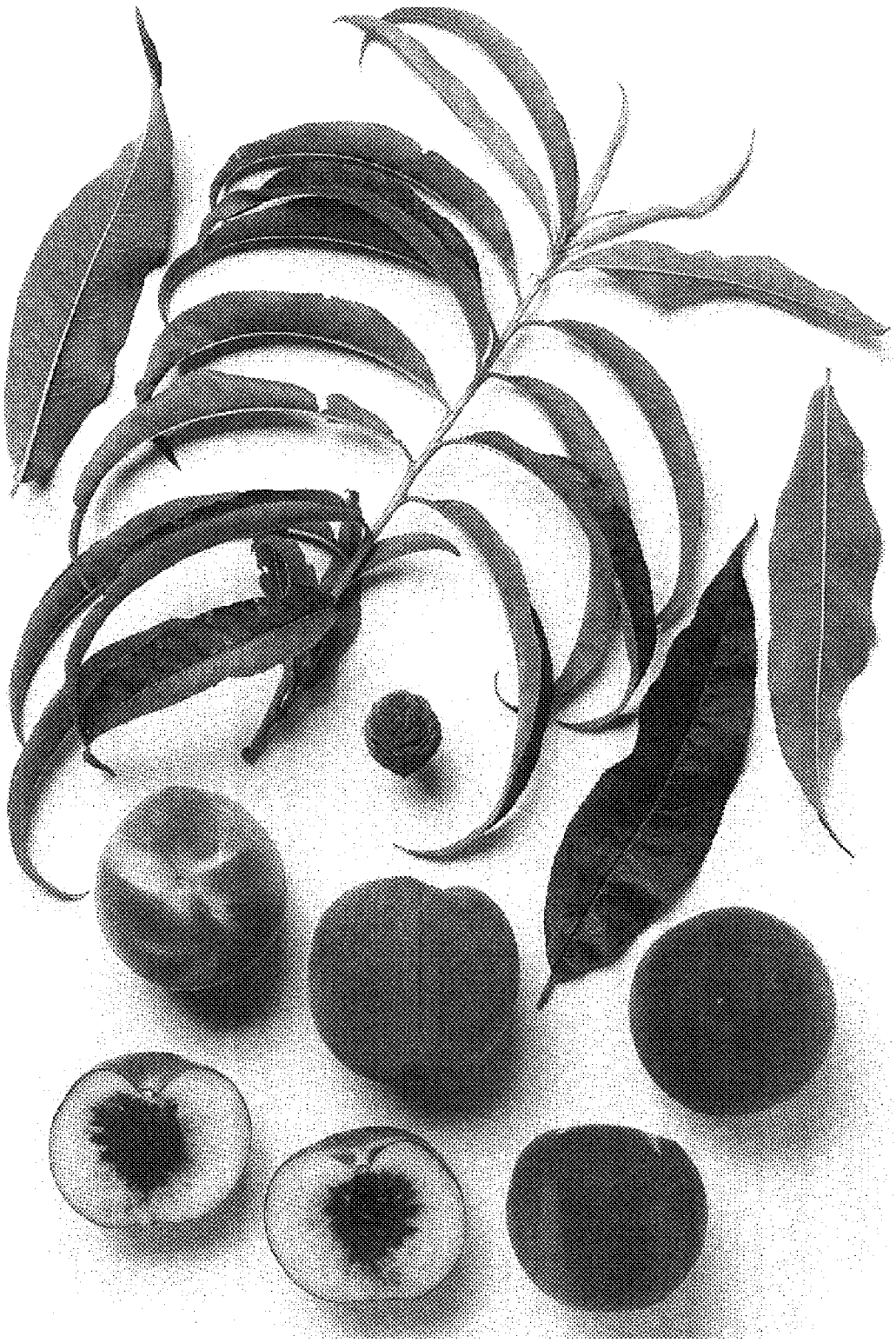
FIG. 1 illustrates, clockwise from top left: the front and back of whole leaves, whole leaves on a twig from a twig end, top, bottom and side views of the fruit displaying the characteristic skin color and shape, fruit cut in half displaying the flesh, pit cavity and pit in place, and pit.

Referring more specifically to the horticultural details of the new and distinct variety of peach tree, the following descriptions have been observed under the ecological conditions prevailing at the origin orchard, which is located near Kerman, Calif. in the San Joaquin Valley of Central California. All major color designations are by reference to the "Dictionary of Color" by Maerz and Paul, First Edition, published in 1930. Common colors are also employed.

Tree:

*Size.*—Medium, for 3rd leaf tree, 10–11 feet high, 8–9 feet width.

*Vigor.*—Very good.

*Shape.*—Upright and spreading.

*Productivity.*—Very good to excellent for 3rd leaf tree with regular bearing.

*Chilling requirements.*—Normal weather factors, including temperatures and rainfall at that time of year, for peach trees in the Central San Joaquin Valley in California.

Trunk:

*Size.*—Medium — 15 inches in circumference, 12 inches above ground.

*Surface texture.*—Moderately rough.

*Color code.*—PL.56 E8 Burgundy.

*Lenticels.*—Scattered — moderate number.

*Size.*—Small — 0.04 inch.

Branches:

*Size.*—Medium, circumference 7 inches, 17 inches above crotch-angle of branches approximately 60°.

*Surface texture.*—Mature — nearly smooth. Immature — smooth.

*Color code (1 year or older).*—Pl.1.7 E9—Kaffa, Hamstead Brown.

*Color code (immature).*—Pl1.20 K6 — Piquant green.

*Lenticels.*—Number — sparse. Size — small — less than 0.04 inch.

Leaves:

*Size.*—Medium-large.

*Length.*—6.65–7.72 inch.

*Width.*—1.18–1.89 inch.

*Shape.*—Lanceolate.

*Color code.*—Upwardly disposed surface — Pl.24 C10 — Shirvan. Downwardly disposed surface — Pl.22 L7 — Art. Green.

*Marginal form.*—Crenate.

*Leaf vein.*—Color code — Pl.19 L5 — Cosse gr. Thickness — 0.04 inch.

*Glandular characteristics.*—None.

*Petiole.*—a. Size — medium. b. Length — 0.39–0.55 inch. c. Thickness — 0.08 inch. d. Color Code — Pl. 19 D6 — Pistachio gr. or Pistache.

*Stem glands.*—Form — reniform. Postioin — 1 long gland on left, 0.16 inch and 2 on right, 0.04–0.08 inch. Color Code — Pl.6 E9 Near Cameo Br.

*Stipules.*—One 0.08 inch Pl.7 J12 — Chutney.

Flowers:

*Blooms per cluster.*—Approximately three (3) to four (4) flowers in a cluster.

*Flower buds.*—Conic shape. Color Code — Pl.1 C4 Sweet Bryer.

*Date of first bloom.*—50% — Feb. 26, 2005 — showy, abundant.

*Calyx.*—5 sepals. Color Pl.7 L6 India Red.

*Flower diameter size.*Large — 1.65–1.8 inch.

*Petal shape.*—Obovate, minor overlapping.

*Petals.*—5. Size — Length — 0.78–0.82 inch. Width — 0.75–0.98 inch.

*Color.*—Pl.1 C1 Light Pink.

*Claws.*—Small — 0.08 inch.

*Petal margins.*—Undulate.

*Pedicel.*—0.12 inch — Color — Pl.19 L6 Calliste green.

*Sepals.*—Size — 0.20 inch to 0.26 inch.

*Stamen.*—33–38. Average Number of Stamens — 36. Average Length of Stamens — 0.48 inch.

*Filament.*—Color — Pl.1 J8 Geranium Pink. Length — 0.35–0.67 inch.

*Anthers.*—Small — Color — Pl.7 H9 Liver Br.

*Pistil.*—0.91 inch.

*Fertility.*—Self fertile — no pollinator required.

*Pollen.*—Color — yellow gold Pl.9 L3.

Fruit:

*Average weight of fruit.*—198.8 grams (70 oz.).

*Date of maturity.*—July 13–20.

*Size.*—Diameter Axial Plane — 2.40–3.03 inches. Transverse in Suture Plane — 2.64–2.87 inches. Transverse at Right Angles to Suture Plane — 2.40–2.56 inches.

*Form.*—Symmetrical or Asymmetrical — slightly asymmetrical. Suture — slightly on ventral side, more prominent on distal side. Ventral Surface — smooth.

*Stem cavity.*—Width — 0.51–0.98 inch. Depth — 0.39–0.83 inch. Length — 1.10–1.38 inch. Shape — ovate.

*Stem.*—Length 0.31–0.39 inch. Caliper — 0.16 inch.

*Apex.*—Rounded.

*Pistil point.*—Very small and not prominent.

*Skin.*—Thin — normal for freestone peach.

*Texture.*—Lightly pubescent.

*Ovary.*—Bare.

*Tendency to crack.*—None known.

*Color code.*—Blush Color — Pl.41 L6 — shade of red. Ground Color — Pl.11 L3 Canary, Quince Y. Flesh color — Pl.11 L5 Lime Y with Red Flesh (Pl.49 L7) Indiana. Color of Surface or Pit Near Pit Cavity — Pl.49 L7 Indiana. Color of Pit Well — Pl.49 H5 — Valencia.

*Juice production.*—Moderate.

*Flavor.*—Very good.

*Aroma.*—Mild.

*Pit cavity fibers.*—Numerous on both sides of pit cavity — total approximately 30.

*Texture.*—Somewhat stringy.

*Ripening.*—Even.

*Eating quality.*—Very good.

Stone:

*Free or cling.*—Freestone.

*Pit fibers.*—Numbers — few. Length — short, 0.12–0.16 inch.

*Size.*—Length — 1.18 inch. Width — 0.98 inch. Thickness — 0.79 inch.

*Form.*—Ovate.

*Hilium.*—0.20 inch.

*Apex shape.*—Slightly rounded.

*Color code (dry).*—Pl.55 L8 Rubient.

*Base.*—Slightly rounded.

*Sides.*—Heavily grooved.

*Ridges.*—On both sides from apex to base.

*Tendency to split.*—Approximately 10 to 15% split ripe.

*Use.*—Fresh market.

*Keeping and shipping quality.*—Very good.

*Resistance to disease.*—Not known.

*Harvesting.*—Between July 13–20 in the San Joaquin Valley of Central California.

What is claimed is:

1. A new and distinct variety of peach tree having characteristics described and illustrated herein.

* * * * *